United States Patent [19]

Widra

[11] Patent Number: 4,570,629

[45] Date of Patent: Feb. 18, 1986

[54] HYDROPHILIC BIOPOLYMERIC COPOLYELECTROLYTES, AND BIODEGRADABLE WOUND DRESSING COMPRISING SAME

[75] Inventor: Abe Widra, River Forest, Ill.

[73] Assignee: University of Illinois Foundation, Urbana, Ill.

[21] Appl. No.: 534,486

[22] Filed: Sep. 21, 1983

Related U.S. Application Data

[63] Continuation-in-part of Ser. No. 358,994, Mar. 17, 1982, abandoned.

[51] Int. Cl.$^4$ ............................................... A61M 5/20
[52] U.S. Cl. ...................................... 128/156; 604/368
[58] Field of Search ................ 128/155, 156; 604/368

[56] References Cited

U.S. PATENT DOCUMENTS

| | | | |
|---|---|---|---|
| 3,483,289 | 12/1969 | Michaelson et al. | 424/36 |
| 3,655,416 | 4/1972 | Vinson et al. | 424/36 |
| 4,060,081 | 11/1977 | Yannas et al. | 128/156 |
| 4,066,512 | 1/1978 | Lai et al. | 424/2 |
| 4,074,366 | 2/1978 | Capozza | 3/1 |
| 4,178,361 | 12/1979 | Cohen et al. | 424/81 |
| 4,195,077 | 3/1980 | Marsh et al. | 424/359 |
| 4,264,493 | 4/1981 | Battista | 424/359 |
| 4,287,177 | 9/1981 | Nakashima et al. | 424/DIG. 13 |
| 4,344,967 | 8/1982 | Easton et al. | 424/359 |
| 4,347,234 | 8/1982 | Wahlig et al. | 424/36 |
| 4,378,017 | 3/1983 | Kosugi et al. | 424/36 |

*Primary Examiner*—C. Fred Rosenbaum
*Assistant Examiner*—Sherri E. Vinyard
*Attorney, Agent, or Firm*—Barbara A. Shimei

[57] ABSTRACT

Hydrophilic biopolymeric copolyelectrolytes comprising (a) a water-soluble linear anionic protein polyelectrolyte component derived from keratin and (b) a water-soluble linear cationic biopolymer polyelectrolyte component derived from at least one biopolymer selected from the group consisting of collagen and a glucosaminoglycan. Hydrogel membranes formed from the copolyelectrolytes are useful as biodegradable dressings for denuded tissue wound sites.

39 Claims, No Drawings

HYDROPHILIC BIOPOLYMERIC COPOLYELECTROLYTES, AND BIODEGRADABLE WOUND DRESSING COMPRISING SAME

This application is a continuation-in-part of copending U.S. patent application Ser. No. 358,994, filed Mar. 17, 1982 now abandoned.

BACKGROUND OF THE INVENTION

This invention relates to novel hydrophilic biopolymeric materials and, more particularly, to the use of such materials in the form of hydrogel membranes as biodegradable dressings for denuded tissue wound sites such as burn wounds and ulcerations.

In the therapeutic procedure for treating an extensively burned patient, devitalized tissue is removed from the burn site, and the debrided areas are covered with a temporary burn wound dressing prior to definitive autografting. The temporary burn wound dressing ideally provides several important therapeutic functions. First of all, it serves as a barrier to prevent loss of water, salts, and proteins from the internal milieu while blocking microbial infection from the environment. Secondly, it serves to improve wound bed base and promote wound closure, thereby facilitating decontamination and regeneration of the wound area. Thirdly, it serves to alleviate pain.

The best wound coverage material is skin itself—a biologic dressing with a collagenous component rendering it adherent to endogenous fibrin, and a keratinized water proof surface. Biologic dressings in current use include commercially available pigskin heterograft, and living (donor) human or human cadaver homograft material. While human skin has a number of advantages over pigskin for this purpose, there are many problems associated with obtaining, storing, and using frozen and lyophilized human skin. Skin banks require at least 200 cadavers per year in order to supply existing burn centers. In any case, either of these types of biologic dressings give rise to rejection phenomena which mandate their removal and replacement every 2 to 5 days, or every 2 to 3 weeks if measures are taken to retard the rejection phenomenon. Eventually, however, these dressings must be stripped, often resulting in bleeding and renewed destruction of the graft base.

The body's rejection of foreign biologic dressings has lead to a search for skin substitutes which are either completely synthetic, derived from tissue components, or some combination thereof. Such search has not heretofore met with great success due to the difficulties involved in finding a material exhibiting the proper combination of properties essential for an ideal skin substitute. These properties include rapid, uniform, and strong adherence of underlying tissues; water vapor transport characteristics sufficient to keep the underlying tissues moist without creating pooling; elasticity; durability; intact bacterial barrier characteristics; nonantigenicity and nontoxicity; high permeability to oxygen; capability of being easily applied and removed; easily storable; and relatively inexpensive.

The materials previously proposed as skin substitutes have generally been found to be lacking in one or more of the foregoing properties. The most satisfactory of these materials have consisted of layered composite membranes having an outer layer designed for durability and elasticity, such as silicone or other synthetic polymeric film; and an inner layer designed for maximum adherence, such as collagen, cotton gauze, or Dacron flocking. However, the necessity for these composite membrane burn wound dressings to be stripped from the wound prior to definitive autografting, poses some difficult design problems. Since these dressings generally depend upon tissue ingrowth into their inner layer for adherence to the wound, complete removal of the dressing is difficult and may require redebridement before grafting. While it may be possible to overcome this problem by having the inner layer formed of a biodegradable material, such approach has been found to result either in a premature loss of adherence and effectiveness of the dressing before completion of wound healing, or in the formation of considerable scar tissue, unless the biodegradation rate of the inner layer is carefully controlled so as to precisely coincide with the rate of wound healing.

Homogeneous hydrogel membranes formed from the hydrophilic synthetic polymeric material, Hydron, have also been proposed as skin substitutes for use as burn wound dressings. This material combines adherency to dry and moist tissue with the other desirable properties of conformability to a regular contour, elasticity, nonantigenicity, being inert, and providing an effective antimicrobial barrier. Its major drawbacks as a burn wound dressing, however, are its excessive permeability to water and its low degree of durability when washed with water or in the presence of moderate oozing or bleeding. Moreover, its elasticity is too rapidly lost upon drying. For these reasons, it has not proven to be practical for relatively long-term burn wound dressing applications.

SUMMARY OF THE INVENTION

It is, accordingly, a primary object of the present invention to provide a novel material exhibiting the proper combination of properties rendering it suitable for use as a dressing for burn wounds and other denuded tissue wound sites, including deep ulcers.

Another object of the invention is to provide a novel wound dressing material which is adherent to denuded tissue, elastic, durable, and completely biodegradable so as to eliminate the necessity for its being stripped from the wound site.

A further object of the invention is to provide a novel wound dressing material in accordance with the preceding objects, which is absorbent to wound exudates without losing its durability, and which has water vapor transport characteristics sufficient to keep the underlying tissues moist without creating pooling.

Still another object of the invention is to provide a material in accordance with the preceding objects, which is homogeneous.

A still further object of the invention is to provide a material in accordance with the preceding objects, which can be easily and conveniently applied to burn wounds, ulcers, and other denuded tissue wound sites.

The above and other objects are achieved in accordance with the present invention by providing novel hydrophilic biopolymeric copolyelectrolytes comprising (a) a water-soluble linear anionic protein polyelectrolyte component derived from keratin and (b) a water-soluble linear cationic biopolymer polyelectrolyte component derived from at least one biopolymer selected from the group consisting of a glucosaminoglycan and collagen.

Hydrogel membranes comprising the copolyelectrolytes of the present invention exhibit a combination of properties rendering them useful as biodegradable dressings for burn wounds and other denuded tissue wound sites. Such membranes are strongly adherent to underlying tissues, elastic, durable, highly permeable to oxygen, absorbent to wound exudates without losing their durability, have water vapor transport characteristics sufficient to keep the underlying tissues moist without creating pooling, and have intact bacterial barrier characteristics. They may be readily and conveniently applied to the wound site in several alternative modes. By virtue of their biodegradability, they do not require stripping. In the latter stages of wound healing, when moisture through the wound area is much reduced, any remaining copolyelectrolyte material will dry and harden to a protective carapace, which will fall off naturally without leaving any scarring.

DESCRIPTION OF PREFERRED EMBODIMENTS

The hydrophilic biopolymeric copolyelectrolytes of the present invention are water-insoluble, water-swellable materials comprising a water-soluble linear anionic protein polyelectrolyte component derived from keratin and a water-soluble linear cationic biopolymer polyelectrolyte component derived from at least one biopolymer selected from the group consisting of a glucosaminoglycan, such as chitosan, and the protein, collagen. Keratin is a protein obtained from sources such as skin, fur, hair, wool, horn, nails, claws, beaks, and scales. It may be readily isolated from its source material and separated into its alpha-keratose and gamma-keratose fractions by procedures well known in the art, such as, for example, as described by Widra, Mycopathologia et Mycologia Applicata, Volume 30, pages 141–144 (1966) and Rhodes, et al., Mycopathologia et Mycologia Applicata, Volume 33, pages 345–348 (1967), incorporated herein by reference. Chitosan is the deacylated form of chitin, which is a glucosaminoglycan obtained as a major constituent of the shells of shrimp, crabs, and lobsters, the cell walls of filamentous fungi, and the exoskeletons of insects. Chitosan is commercially available in the form of fibers, for example, from Sigma-Aldrich Corporation, St. Louis, Mo. Collagen is a fibrous protein which comprises the major portion of the white fiber in connective tissues of the animal body, particularly in the skin, bones and tendons. It is commercially available in the form of soluble fibers, for example, from Sigma-Aldrich Corporation, St. Louis, Mo.

The water-soluble derivatives of keratin employed in the anionic polyelectrolyte component of the copolyelectrolytes of the present invention are linear polyelectrolytes in which the keratin moiety is in anionic form. A particularly suitable anionic keratin polyelectrolyte is ammonium keratinate, obtained as the total ammonium hydroxide-soluble fraction of peracetic acid-oxidized human hair, or the alpha-keratose component of this fraction, by the procedures described in the aforementioned Rhodes, et al., article. Due to evidence indicating a higher degree of nonantigenicity, the alpha-keratose form of ammonium keratinate is preferred.

The water-soluble derivatives of the glucosaminoglycan and collagen employed in the cationic biopolymer polyelectrolyte component of the copolyelectrolytes of the present invention are linear polyelectrolytes in which the biopolymer moiety is in cationic form. Particularly suitable cationic glucosaminoglycan and collagen polyelectrolytes are the carboxylates of these biopolymers, such as their acetates or citrates, obtained by dissolving the biopolymer in an aqueous solution of the corresponding carboxylic acid. Chitosan acetate, collagen acetate, and mixtures thereof, are preferred for use in the cationic biopolymer polyelectrolyte component.

The weight ratio of the anionic keratin polyelectrolyte component to the cationic biopolymer polyelectrolyte component in the copolyelectrolytes of the present invention may vary over a rather wide range, and is most suitably within the range of from about 0.001:1 to about 16:1 and more preferably within the range of from about 0.001:1 to about 7:1. When the cationic biopolymer polyelectrolyte component is a mixture of the glocosaminoglycan and collagen, the weight ratio of the glucosaminoglycan to collagen is preferably within the range of from about 0.5:1 to about 13:1, and more preferably within the range of about 3:1–10:1.

When the water-soluble anionic keratin polyelectrolyte component is contacted in the presence of water with the water-soluble cationic biopolymer polyelectrolyte component (i.e., cationic glucosaminoglycan, cationic collagen, or mixtures thereof), the polyelectrolyte components spontaneously rearrange themselves into a water-insoluble, water-swellable solid coherent maass. While the precise mechanism of reaction resulting in the formation of these biopolymeric copolyelectrolyte hydrogels is not known with certainty, it is believed that the initial attraction between the two polyelectrolyte components is due to their opposite net charge, and that closer juxtaposition of the biopolymer molecules then brings into play a variety of steric fitting and chemical bonding and crosslinking mechanisms at multiple sites along the molecules to produce interdigitating cobiopolymers. In any event, their properties and characteristics are totally different from those of their individual components.

In their hydrated form, the biopolymeric copolyelectrolytes of the present invention are stress-durable hydrogels which may be manipulated like a self-annealing paste or putty and thereby formed into membrane sheets, troweled into crevices, or formed in shaped containers or around glass or metal or through perforations. As long as moisture is present, they remain flexible and elastic. As they dry down, they shrink, adhere to flat surfaces, self-anneal and harden to a crystallite form of packed microfibrils. Since they are permeable to and expansible in water, the copolyelectrolytes may be regenerated by the addition of water from their dehydrated form to their hydrogel form, and thereafter reshaped.

Preparation of the biopolymeric copolyelectrolytes of the present invention may suitably be carried out by mixing together aqueous solutions of the anionic keratin polyelectrolyte component and the cationic biopolymer polyelectrolyte component to precipitation end-point and allowing the resulting integral mixture to dry down to a cohesive membrane. This may be done very carefully in vivo. Alternatively, aqueous solutions of the anionic keratin polyelectrolyte component and the cationic biopolymer polyelectrolyte component may be mixed to form a gel which is then applied to the wound and allowed to dry down to form the cohesive membrane. Yet another alternative is to mix aqueous solutions of the anionic keratin polyelectrolyte component and the cationic biopolymer polyelectrolyte component to form a hydrogel which is allowed to dry on a mold or form; the membrane may then be removed from its forming substrate either by cracking it off in its brittle dehydrated state and forming it into a powder, or by teasing and floating it off in water as a flexible hydrogel membrane. The optimal weight ratio of the anionic keratin polyelectrolyte component to the cationic biopolymer polyelectrolyte component in copolyelectrolytes made by these mixing methods is about 0.2:1 to about 7:1; a range of from about 0.4:1 to about 3.75:1 is preferred.

As an alternative preparative procedure, one of the polyelectrolyte components in solid form may be contacted with an aqueous solution of the other polyelectrolyte component. For example, the cationic biopolymeric polyelectrolyte component in solution may be dried down to a crystalline complex which resembles cellophane sheeting, its thickness and strength varying with the amount of solution used to cover a given area before dry-down. Contacting the cationic biopolymeric polyelectrolyte sheeting with an aqueous solution of ammonium keratinate results in the formation of a copolyelectrolyte hydrogel membrane. This may be accomplished, for example, by swabbing or spraying the ammonium keratinate solution onto both sides of a sheet of cationic biopolymeric polyelectrolyte component and allowing the wetted sheet to dry. Alternatively, the ammonium keratinate solution may be swabbed or sprayed onto one side of a first sheet of cationic biopolymeric polyelectrolyte component; the wetted side of this sheet is then overlaid with a second sheet of cationic biopolymeric polyelectrolyte component which may be the same or different from the first sheet. This process may be repeated to form a multiple "sandwich" membrane. In yet another embodiment of this invention, the ammonium keratinate solution is first sprayed or swabbed directly onto the open wound which is then overlaid with a sheet of cationic biopolymeric polyelectrolyte component to form a copolyelectrolyte hydrogel membrane in situ. In each of these alternate embodiments the optimal weight ratio of the anionic keratin polyelectrolyte component to the cationic biopolymeric polyelectrolyte component is about 0.001:1 to about 0.2:1. Expressed in more convenient terms, about 30–500 mg anionic keratin polyelectrolyte is applied per 1000 sq. cm. surface area of the cationic biopolymeric polyelectrolyte component sheeting.

The biopolymeric copolyelectrolytes may be formulated with various additives, such as, for example, plasticizers or softening agents, antibiotic, antifungal or other pharmaceutical agents, cells, enzymes, antibodies, pigments, or the like, to enhance their properties for a particular end use. Such additives may suitably be incorporated into the copolyelectrolytes either subsequent to their formation or along with one or more of their polyelectrolyte components during their formation. When used in wound dressing applications, for example, the biopolymeric copolyelectrolytes preferably are mixed with a non-toxic plasticizer or softener, such as glycerol, in an amount sufficient to enhance the flexibility and/or adhesion of the dressing. When employing chitosan acetate sheeting as one of the polyelectrolyte components in formulating the biopolymeric copolyelectrolytes, the plasticizer or softener is advantageously incorporated into the chitosan acetate sheeting, for example, in a weight ratio of plasticizer or softener to chitosan acetate within the range of from about 0.5:1 to about 12:1.

The hydrogel membranes in accordance with the present invention may be formed in a wide range of thicknesses, the optimum thickness varying with the desired end use. Membrane thicknesses of at least about 1 mil will have sufficient strength and durability for most application. For membranes used as wound dressings, a thickness ranging from about 1 to about 7 mils has been found to be particularly suitable. The membrane thickness may suitably be controlled in various ways. For example, varying the concentrations of the polyelectrolyte components in the stock solutions employed in the formation of the copolyelectrolytes will result in corresponding variations in the resulting membrane thickness. Alternatively, separately formed hydrogel layers may be laminated together, for example, with the aid of an intermediate coating of a suitable softener or plasticizer (e.g., a glycerol-water mixture), thereby forming a composite hydrogel membrane. Such composite membranes may be fabricated with their separate hydrogel layers having either the same or different composition. For example, the cationic biopolymer polyelectrolyte component of the copolyelectrolyte may be cationic chitosan in one layer and cationic collagen in another layer.

The combination of properties exhibited by the biopolymeric copolyelectrolyte hydrogel membranes of the present invention render them particularly suitable for use as dressings for burn wounds and other denuded tissue wound sites. Such membranes are rapidly, uniformly, and strongly adherent to underlying tissues by virtue of their shrinkdown from the fully hydrated state and/or by virtue of their collagen content and resulting linkage to fibrin in the wound bed. They are durable to physical stress and may be thickened as needed to enhance their durability. They have a high degree of absorbancy for serous or bloody exudate, and remain flexible and elastic so long as moisture is present. Their water vapor transport characteristics are such as to allow pervaporation of water at a rate sufficiently high so as to prevent fluid pooling beneath the dressing, and yet sufficiently low so as to maintain the requisite moisture at the wound surface for wound healing cell migration to occur and the requisite moisture within the membrane for maintenance of flexibility and elasticity. The hydrogel membranes are highly permeable to oxygen, allowing air to get into the wound while stopping bacteria. Their microbial barrier function can be further improved by incorporating antimicrobial agents into the dressing, for example, by inclusion in the hydrogel during its formation, by inclusion between hydrogel layers, or by direct spraying or smearing onto the wound dressing as clinical conditions demand.

The materials used in making the copolyelectrolytes and their hydrogel membranes are non-antigenic and non-toxic, and are readily available. Furthermore, the copolyelectrolytes, either in dehydrated or hydrated form, are easily storable at room temperature in polyethylene bags, aluminum foil packs, or plastic dishes after autoclaving, gas, alcohol, or radiation sterilization. Sterilization by ultraviolet radiation or ethylene oxide gas is preferred.

The copolyelectrolyte hydrogel membrane wound dressings may be readily and conveniently applied to the wound site in several different application modes. For example, the hydrogel may be preformed and applied to the wound site either as a preformed membrane or as a self-annealing paste. Alternatively, the copolyelectrolyte may be preformed and applied to the wound site in dehydrated form, either as a dried membrane or as a powder, and thereafter allowed to hydrate to an adherent conforming hydrogel membrane in situ on the wound site. A further alternative application mode is to individually apply the anionic keratin polyelectolyte component and the cationic biopolymer polyelectrolyte component to the wound site so as to effect in situ formation on the wound site of the copolyelectrolyte as a hydrogel membrane. In this latter mode of application, both of the polyelectrolyte components may be applied as aqueous solutions, or one may be applied as an aqueous solution and the other in solid form. For example, the wound site may be first sprayed or swabbed with an aqueous solution of ammonium keratinate, and thereafter overlaid with dried chitosan acetate sheeting, preferably including a flexibility-and/or adhesion-enhancing amount of a non-toxic plasticizer or softener, such as glycerol.

The copolyelectrolyte hydrogel membrane wound coverings can remain in place over substantially the entire wound healing period, during which time fluid exudate from the wound is absorbed, and white blood cells and macrophages infiltrate the hydrogel and ultimately dry at the upper air interface to form a protective scab, while entering fibroblasts elaborating collagen fibers bind to the lower moist surface of the membrane. Epidermal cells move in centripetally from the edge of the wound through these collagen fibers to grow over and close the wound in the moist space between the fibroblasts and the white cell-infiltrated membrane. The moist membrane becomes biodegraded by the skin cells, white cells and macrophages. In the latter stages of wound healing, when moisture through the wound area is much reduced, the remaining membrane will dry and harden to a protective carapace or scab, which will fall off naturally without leaving any scarring. The dried scab may, if desired, be softened and removed by application of a glycerine-water mixture.

While the hydrophilic biopolymeric copolyelectrolytes of the present invention have been described primarily with reference to their utility as hydrogel membrane wound dressings, it will be understood that these novel materials have a wide variety of other potentially important applications. For example, they may be used in conjunction with implantable prosthetic devices, and as scar tissue coverings, sutures, tapes, sustained release drug carriers, and tube linings in bypass surgery. They may be covered with an overgrowth of a layer or layers of cultured epithelial cells to form a synthetic skin wound dressing or graft, or for use as a lining in prosthetic implants and devices.

The invention is further illustrated by way of the following examples.

EXAMPLE 1

Stock solutions for use in preparing hydrophilic biopolymeric copolyelectrolytes in accordance with the present invention were prepared in the following manner.

Chitosan acetate solution was prepared by continuously stirring 500 mg of practical grade shrimp chitosan fibers (Sigma-Aldrich Corporation, St. Louis, Mo.) into 100 ml of cold 0.25% (v/v) acetic acid. The solution was cleared of gross particulate matter by filtration through a 12-layer gauze pad on a Buchner funnel.

Collagen acetate solution was prepared by stirring 200 mg of bovine collagen fibers (acid-soluble Type III, Sigma-Aldrich Corporation, St. Louis, Mo.) in 100 ml of cold 0.25% (v/v) acetic acid.

Alpha-keratose ammonium keratinate solution was prepared as follows. Twelve grams of clean, dry, blond human hair, previously degreased and washed, were placed in a 1 liter Erlynmeyer flask containing 320 ml of water. 80 ml of concentrated peracetic acid was added, and the flask stoppered. The contents of the flask were swirled and then placed in a refrigerator for 24 hours with occasional swirling. The bleached, easily stretched and torn ("retted") hair was then freed of the peracetic acid by decantation and thorough washing with separate water rinses. The washed retted hair was then covered with 800 ml of 3N ammonium hydroxide, and stirred in the cold for 24 hours to solubilize hair keratins. The total soluble protein (TP) fraction was then cleared of solids by centrifugation, and discarding undissolved protein and non-protein residual debris. The TP fraction was further clarified through Whatman No. 1 paper, dialyzed against water until the dialyzate wash gave only a faint positive for ammonia with Nessler's reagent, and then Seitz microfiltered. Alpha-keratose was precipitated from the TP fraction by incremental addition of 0.1N hydrochloric acid while stirring. The precipitate was collected by centrifugation, and the supernatant gamma-keratose, antigenic for rabbits, was discarded. The alpha-keratose precipitate was washed in water, re-centrifuged, and then solubilized in 0.1N ammonium hydroxide. A second cycle of precipitation, washing, and solubilization was run on the alpha-keratose before final dialysis against water, concentration of the protein microfiltration, and storage in a sterile container. The resulting solution contained approximately 7.5 mg of alpha-keratose ammonium keratinate per ml.

EXAMPLE 2

The collagen acetate and alpha-keratose ammonium keratinate stock solutions prepared in Example 1, were employed in the preparation of a collagen keratinate copolyelectrolyte. 10 ml of the collagen acetate solution (containing 20 mg of collagen acetate) and 10 ml of the ammonium keratinate solution (containing 75 mg of alpha-keratose ammonium keratinate) were mixed together in a plastic Petri dish to precipitation end-point. Upon evaporation of the supernatant, the precipitate dried down into a dry crystalline-like sheet. Upon adding water to the dried down precipitate, a self-annealed flexuous, diaphanous, cohesive collagen keratinate copolyelectrolyte hydrogel membrane was formed, which was teased and floated from the bottom of the dish.

EXAMPLE 3

The chitosan acetate and alpha-keratose ammonium keratinate stock solutions prepared in Example 1, were employed in the preparation of a chitosan keratinate copolyelectrolyte. Fifty mg of chitosan acetate solution (containing 250 ml of chitosan acetate) and 15 ml of the ammonium keratinate solution (containing 112.5 mg of alpha-keratose ammonium keratinate), were mixed together in a plastic Petri dish to precipitation end-point to produce an opaque whitish, sticky, flocculent precipitate. Upon evaporation of the supernatant, the precipitate dried down to form a hard brittle translucent sheet, which was pried or cracked from the bottom of the dish. Upon adding water to the dried material, a self-annealed, tough, stretchable, cuttable, cohesive chitosan keratinate copolyelectrolyte hydrogel membrane was formed.

EXAMPLE 4

All three of the stock solutions prepared in Example 1 were employed in the preparation of a chitosan-collagen keratinate copolyelectrolyte. 30 ml of the chitosan acetate solution (containing 150 mg of chitosan acetate), 10 ml of the collagen acetate solution (containing 20 mg of collagen acetate), and 10 ml of the ammonium keratinate solution (containing 75 mg of alpha-keratose ammonium keratinate), were mixed together in a plastic Petri dish to precipitation end-point. Upon evaporation of the supernatant, the precipitate dried down to a crystalline-like sheet. Upon adding water to the dried down precipitate, a self-annealed, flexible, cohesive chitosan-collagen keratinate copolyelectrolyte hydrogel membrane was formed, which was teased and floated from the bottom of the dish.

EXAMPLE 5

This example illustrates the preparation of a chitosan keratinate copolyelectrolyte hydrogel membrane employing solid chitosan acetate sheeting as the cationic chitosan polyelectrolyte component.

Chitosan acetate sheeting was prepared by mixing together 2 ml of glacial acetic acid, 4 ml of glycerol, 794 ml of water, and 4 g of practical grade shrimp chitosan fibers (Sigma-Aldrich Corporation, St. Louis, Mo.). The mixture was stirred until a solution was formed. The solution was filtered through five layers of cheese cloth, poured into a flat pan, and allowed to dry down to form a flexible, sticky, cohesive solid sheet of chitosan acetate (approximately 9"×12").

When the chitosan acetate sheeting was sprayed on both sides with a total of 10 ml (75 mg) of the alpha-keratose ammonium keratinate stock solution prepared in Example 1, the solid sheeting swelled to form a self-annealed, flexible, cohesive chitosan keratinate copolyelectrolyte hydrogel membrane.

EXAMPLE 6

Examples 6, 7, and 8 illustrate the preparation of chitosan keratinate copolyelectrolyte hydrogel membranes containing a variety of antibiotics.

Chitosan acetate sheeting was prepared by mixing 2 ml glacial acetic acid, 2 ml glycerol, 40,000 µg gentamycin sulfate (Garamycin, Schering Corp., Kenilworth, NJ), 796 ml water, and 4 g practical grade shrimp chitosan fibers (Sigma-Aldrich Corporation). The mixture was stirred to solution, filtered, and dried as in Example 5.

The 9"×12" dried chitosan acetate sheeting was sprayed on both sides with a total of about 10 ml of a 5 mg/ml alpha-keratose ammonium keratinate solution prepared in a manner analogous to Example 1, to form a chitosan keratinate copolyelectolyte hydrogel membrane containing the representative antibiotic gentamycin sulfate.

EXAMPLE 7

Chitosan acetate sheeting was prepared by mixing 2 ml glacial acetic acid, 2 ml glycerol, 796 ml water, and 4 g practical grade shrimp chitosan fibers (Sigma-Aldrich Corporation). The mixture was stirred to solution and filtered as in Example 5.

Seventy ml of this chitosan acetate solution was poured into a standard plastic Petri dish (3.5" diameter) and 300 mg demeclocycline powder (Declomycin, Lederle Laboratories Div. American Cyanamid Corp., Wayne, NJ) was added with stirring. The mixture was allowed to dry down to a membrane which was then lifted out and sprayed on both sides with a total of 3 ml of a 5 mg/ml alpha-keratose ammonium keratinate solution prepared in a manner analogous to that of Example 1, to form a chitosan keratinate copolyelectrolyte hydrogel membrane containing the representative antibiotic demeclocycline.

EXAMPLE 8

Chitosan acetate sheeting was prepared by mixing 2 ml glacial acetic acid, 2 ml glycerol, 796 ml water, and 4 g practical grade shrimp chitosan fibers (Sigma-Aldrich Corporation). The mixture was stirred to solution and filtered as in Example 5.

Fifty eight ml of this chitosan acetate solution was poured into a standard plastic Petri dish and 1 ml glycerol and 320 mg cefoxitin powder (Mafoxin, Merck Sharp & Dohme, Rahway, NJ), were added with stirring. To this mixture was added 10 ml of a 5 mg/ml alpha-keratose ammonium keratinate solution prepared in a manner analogous to that of Example 1 and containing 125 mg of dissolved tetracycline (Sumycin, Squibb & Sons, Inc., Princeton, NJ). The combined mixture was allowed to dry down to a yellow-brown chitosan keratinate copolyelectrolyte hydrogel membrane containing the representative antibiotics cefoxitin and tetracycline.

EXAMPLE 9

Chitosan acetate sheeting was prepared by mixing 2 ml glacial acetic acid, 2 ml glycerol, 20,000 µg gentamycin sulfate (Valley Biologicals Inc., State College, PA), 796 ml water, and 4 µg practical grade shrimp chitosan fibers (Sigma-Aldrich Corporation). The mixture was stirred to solution, filtered, and dried as in Example 5.

The 9"×12" dried chitosan acetate sheeting was sprayed on both sides with a total of 10 ml of a 5 mg/ml alpha-keratose ammonium keratinate solution prepared in a manner analogous to Example 1 and containing 191 mg dissolved carbenicillin powder (Geocillin, Roerig Div. Pfizer Pharmaceuticals, New York, NY), to form a chitosan keratinate copolyelectrolyte hydrogel membrane containing the representative antibiotics gentamycin sulfate and carbenicillin.

EXAMPLE 10

The ears of a ketamine-anaesthetized 10 pound male New Zealand white rabbit were shorn of hair and prepared for surgery. From the dorsal surface of one ear, a full thickness circle of skin 2.5 cm in diameter was removed, and the wound sponged dry. Sterile alpha-keratose ammonium keratinate solution prepared according to Example 1 was dropped into the wound area and on the surrounding shaven skin. A circular swatch of thin chitosan acetate sheeting (2.4 mg chitosan/cm$^2$) was fitted over the wound area and surrounding skin, resulting in the formation of a chitosan keratinate copolyelectrolyte hydrogel membrane wound dressing, which became tightly bound to all surfaces in a few minutes of drying time. The area was dressed with sterile petrolatum gauze, bandaged and taped. A control ear was also prepared, wherein the wound was dressed only with sterile petrolatum gauze, bandaged and taped.

Examination of the test ear at 10 days postoperation (P.O.) showed a flat scab with normal healing, absorption and disappearance of the copolyelectrolyte hydrogel membrane. The control ear showed normal healing with a central heaped scab. At 14 days P.O., only small residual scabs remained on both ears. During periodic examinations, gauze dressing adherent to the copolyelectrolyte hydrogel membrane was easily separated with a simple saline wash.

EXAMPLE 11

A 10 pound female rabbit was prepared for surgery and a 3.5 cm diameter full thickness of skin was removed from the left flank. The site was then sprayed with sterile alpha-keratose ammonium keratinate solution prepared according to Example 1, and covered with a medium weight chitosan acetate sheet (3.6 mg chitosan/cm$^2$), dressed with petrolatum gauze, bandaged, and taped.

Examinations at 3,7, and 10 days P.O. showed no remarkable changes over the normal healing process. Formation of a capillary net and peripheral ingrowth of new tissue could be observed through the copolyelectrolyte hydrogel membrane "window". Hydrogel membrane overlapping the surrounding normal skin also remained pliable and adherent. Between 10 and 17 days P.O., the lesion had shrunk to 1.9 cm in diameter with the hydrogel membrane absorbed and visible only on edge, sandwiched between the new tissue in the wound area below and a dry scab above. On day 20 P.O., the lesion was further reduced to 1.7 cm in diameter, at which point the experiment was terminated in order to examine the wound site histologically and cytochemically before all the copolyelectrolyte hydrogel membrane was completely absorbed.

EXAMPLE 12

A 10 pound female rabbit was prepared for surgery, and a full thickness of skin removed from a rectangular area 2.5×3.5 cm$^2$. After spraying the wound area with sterile alpha-keratose ammonium keratinate solution prepared according to Example 1, a double layer of chitosan acetate sheeting (two sheets annealed with alpha-keratose ammonium keratinate solution and containing a total of 6.4 mg chitosan/cm$^2$) was applied to the wound and surrounding skin. The area was then dressed with sterile petrolatum gauze, bandaged, and taped.

The copolyelectrolyte hydrogel membrane remained flexible over the moist wound site for 14 days. In drying and contracting over the surrounding skin, the membrane caused puckering, which was relieved by application of a glycerine-water (1:1) solution. Accelerated wound closure with regrowth of fur took place between days 17 and 27 P.O., the area undergoing repair closing to 2×3 cm. The remaining flat membrane surface resembled a hard shell adherent scab under which repair was proceeding. Further bandaging and taping were eliminated as unnecessary for care of the site, and healing was complete 30 days P.O.

EXAMPLE 13

A rabbit was prepared for surgery and a full thickness of skin removed from an approximately square area 4 inches×4 inches. After spraying the area with sterile alpha-keratose ammonium keratinate solution prepared according to Example 1, a double-layered chitosan acetate sheeting similar to that employed in Example 12 was applied to the wound and surrounding skin. The area was then dressed with sterile petrolatum gauze, bandaged, and taped. A control wound of the same approximate size was also prepared, and was dressed only with sterile petrolatum gauze, bandaged, and taped. The wound sites were periodically examined for wound closure. During the first three weeks P.O., wound closure proceeded in the copolyelectrolyte hydrogel membrane-covered wound at a 50% faster rate than in the control wound.

EXAMPLE 14

A goat was prepared for surgery, and full thicknesses of skin were removed from a rectangular area 8 inches×9 inches on one flank and from a rectangular area 7 inches×8 inches on the other flank. The smaller size wound was used as the control, and was dressed only with sterile petrolatum gauze, bandaged, and taped. The larger size wound was sprayed with sterile alpha-keratose ammonium keratinate solution prepared according to Example 1, overlaid with a double-layered chitosan acetate sheeting similar to that employed in Example 12, and then dressed with sterile petrolatum gauze, bandaged, and taped. The two wounds were examined periodically for wound healing and closure. After four days P.O., the copolyelectrolyte hydrogel membrane-covered wound was completely covered with fibroblasts, whereas the control wound showed no signs of healing. After 14 days P.O., the copolyelectrolyte hydrogel membrane-covered wound had closed 2 inches, while the control wound had closed less than 1 inch. After 66 days P.O., the hydrogel membrane-covered wound had been reduced to 1 inch ×3 inches; whereas after 78 days P.O., the control wound had only closed to 2 inches×4 inches.

EXAMPLE 15

Patient A, a 54-year-old white female with multiple left leg ulcers diagnosed as pyoderma gangrenosum secondary to Crohn's disease was seen on Dermatology Service, University of Illinois Hospital, after prior unsuccessful treatment. Two of the ulcer lesions were pre-tibial (a shallow lesion 3" in diameter and an elongated deep crater about 3"×4" long); a third lesion was a deep finger-like ulcer projecting about 1½" into the back of the leg. The patient had been hospitalized for 14 weeks and was receiving high dose prednisone (200 mg daily) for her Crohn's disease and 1% silver nitrate soaks on the ulcers as an antiseptic and to encourage crusting. Silver nitrate was not effective in containing the lesions, nor was a thick zinc oxide paste later applied as an occlusive dressing over the large lesion effective. The patient described accompanying pain as "hot ice picks being driven into the leg".

Only the upper shallow pre-tibial lesion, most resembling the experimental surgical wounds produced in rabbits, was treated at first. The lesion was saturated with a sterile 5 mg/ml solution of alpha-keratose ammonium keratinate prepared in a manner analogous to that of Example 1; thereafter a chitosan sheet [prepared as in the second paragraph of Example 5, but using 2 ml of glycerol] was laid down on the saturated wound surface. This was dressed with a Telfa pad [Kendall Hospital Products Div., Chicago, IL] and gauze. The chitosan sheet absorbed liquid keratinate to form a membrane which adhered to the wound. After 8 days, it was discovered that the wound was infected; the membrane was removed, the wound cleaned, and a chitosan keratinate copolyelectrolyte hydrogel membrane containing gentamycin sulfate prepared according to Example 6 was laid on the ulcer. Obvious success in treatment of the upper shallow ulcer led to gentamycin sulfate chitosan keratinate hydrogel membrane application to the other ulcers with comparable results. Treatment of the deep finger-like ulcer and the large cratered pre-tibial ulcer containing exposed tendon and a small area of exposed bone was then begun. The ulcers were saturated with a sterile 5 mg/ml alpha-keratose solution as above, then overlaid with a UV-sterilized glycerinated chitosan keratinate copolyelectrolyte hydrogel membrane containing gentamycin, prepared according to Example 6. The patient noted absence of tenseness and pain within minutes after the membrane was in place. From this day onward, pre-spraying of lesions with alpha-keratose was discontinued. Instead, the dried-down 9"×12" chitosan acetate sheet was simply peeled from its container form, suspended in air by a set of clips, and sprayed on both sides with a total of 10 ml alpha-keratose (5–7.5 mg/ml) solution prepared according to Example 1, allowed to dry in air, then UV-sterilized under polyethylene (Saran Wrap) sheeting. After about 7 weeks a five-day-old membrane forming a firm carapace on the large lesion had split and lifted off of the healing site which was covered with collagenous fibrotic material. Exudate and drainage into the gauze overwrap was minimal. The patient was ambulatory, free of pain, and discharged from the hospital two weeks later. Follow-up treatment was on an out-patient basis at progressively longer intervals, where soft degraded or hardened non-adherent membrane was simply washed or cut away, the reduced lesion was washed in 3% peroxide, and a new gentamycin sulfate chitosan keratinate copolyelectrolyte hydrogel membrane prepared as above was applied and dressed as usual. Membrane degradation over the collagen-filled granulation base continued for two more months. "Pearling" at the edge of the lesion indicated new epithelial growth. Continued reduction of the lesion by epithelial ingrowth was apparent through the next 6 months to an uneventful recovery with complete reepithelialization.

The successful treatment of these ulcers demonstrates that the membranes of the present invention (1) accelerate healing, (2) cause epidermal closure over a large area, (3) promote healing over a difficult area (i.e., bone), (4) work against a corticosteroid gradient (e.g. high doses of prednisone), and (5) alleviate pain.

EXAMPLE 16

Patient B, a 26 year old black female with progressive systemic scleroderma was seen and treated for painful ankle ulcers on Medical Service, University of Illinois Hospital. She had been unsuccessfully treated during the previous two weeks of hospitalization with whirlpool baths, nitropaste, betadine dressings, and Oxacillin, an oral antibiotic active against the bacteria *Staphylococcus aureus* found in her lesions. The wounds were washed with 3% peroxide, and glycerinated glucosaminoglycan keratinate membranes (prepared according to Example 6 but omitting the antibiotic) were applied to the lesions on each leg with the usual Telfa and gauze overwraps. She was discharged, pain-free, two days later and thereafter continued her treatment as an out-patient in Special Medicine (Rheumatology Service). The initial application of plain membranes did not "take" due to underlying mixed bacteria consisting of *Staphylococcus aureus* and Group B *beta streptococci*.

With application of a chitosan keratinate gentamycin-containing copolyelectrolyte hydrogel membrane prepared as in Example 6, the left ankle lesion incorporated the membrane which was transformed to a scab. It subsequently healed uneventfully. The right ankle lesion remained exudative and now included *enterocci* on culture of exudate. A formulation of the chitosan keratinate copolyelectrolyte hydrogel membrane containing 300 mg of Declomycin, to which the mixed flora were susceptible (prepared as in Example 7) was applied to the wound. It formed an adherent hard scab and remained in place for 8 weeks before cracking and friability allowed bacterial re-entry. The patient is still seen weekly on an out-patient basis, and is currently (8/27/83) wearing a cefoxitin tetracycline-containing glucosaminoglycan keratinate polyelectrolyte hydrogel membrane prepared according to Example 8 over the lesion. Pain is absent.

EXAMPLE 17

Patient C, a 72-year-old white male with a history of rheumatic fever, painful arthritis, a heart valve prosthesis, and an infra-inguinal vessel grafted to treat peripheral vascular insufficiency in his legs had been hospitalized at Lutheran General Hospital, Park Ridge, Ill., when first seen for leg ulcers. The large pre-tibial ulcer (ca. 3"×6") on his left leg was grossly contaminated with mixed *Pseudomonas aeruginosa* and *Staphylococcus aureus*, showed a gangrenous tendon, and was developing a progressive cellulitis traveling toward the knee. A surgical conference group recommended amputation below the knee which was refused by the patient.

The patient was given a single course of amikacin-/prostaphcillin therapy by intravenous drip. No surgical intervention took place. Simultaneously, therapy using 3% peroxide washes followed by application of chitosan keratinate/gentamycin copolyelectrolyte hydrogel membranes prepared according to Example 6 and the usual Telfa and gauze overwraps was initiated. Exudate-wet outer gauze wrapping was changed 2 or 3 times daily. Telfa pads and the chitosan keratinate/gentamycine copolyelectrolyte hydrogel membranes were replaced every 4 or 5 days following a peroxide wash with gauze pad swabbing to remove detritus. Only non-adherent membrane was removed or cut away. The patient was moved to a nursing facility within two weeks where glucosaminoglycan keratinate gentamycin copolyelectrolyte hydrogel membrane therapy was continued. The patient noted absence of pain with the membrane in place. Within 3 weeks the advent of fresh granulation tissue and sealing of the wound edges was apparent. However, continuing destruction of the devitalized tendon was apparent too. The tendon was soft and freely movable while the attending physician expressed pus for bacteriological studies. It was subsequently lifted and painlessly cut out. The Pseudomonas organism proved to be very sensitive to carbenicillin, and so two weeks after surgery the tendon-free lesion was cleaned with peroxide and swabbing, then covered with a gentamycin/carbenicillin-containing chitosan keratinate copolyelectrolyte hydrogel membrane prepared according to Example 9. Carbenicillin-containing solutions polymerize directly and non-uniformly with the glycan solution. Membranes containing carbenicillin must therefore be formulated by spraying the chitosan acetate sheet (in this instance containing gentamycin sulfate) with alpha-keratose solution containing dissolved carbenicillin powder.

Collagen deposition, development of new granulation tissue, and continued ingrowth of peripheral epithelial tissue is taking place in spite of continued exudation from the center of the lesion. Two smaller ulcers, one on the underside of the left leg (1"×2") and one on the inner aspect of the right ankle (1" diameter) were successfully closed with gentamycin-containing glucosaminoglycan keratinate copolyelectrolyte hydrogel membranes prepared according to Example 6.

EXAMPLE 18

Polytetrafluoroethylene (Teflon, E. I. DuPont deNemours and Co., Wilmington, Del.) tubing is used in surgery as a prosthetic device to replace blood vessels. Narrow-bore tubing is extremely prone to thrombus formation. Hence there is much interest and value in obtaining a non-thrombogenic lining for such tubing or better yet, a lining which will support confluent growth of endothelial cells, the natural lining of blood vessels.

Such a lining was prepared by the following procedure: A section of polytetrafluoroethylene (PTFE) tubing (Gore-tex, W. L. Gore and Assoc., Flagstaff, Ariz.) was soaked in absolute ethanol to destroy its hydrophobic properties. The tubing became translucent; excess fluid was drained but the tubing was not allowed to dry completely.

One end of the tubing was pinched closed and a Pasteur pipette was used to fill the tube with a portion of a solution of 2 ml glacial acetic acid, 2 ml glycerol, 796 ml water, and 4 g practical grade shrimp chitosan fibers (Sigma-Aldrich Corporation). The upper end of the filled tube was then stretched gently in order to insure thorough wetting of all pores in the tube. The filled tube was then laid in a horizontal position and allowed to dry down. The tube was rotated once during drying to insure even dry-down. The efficacy of the chitosan acetate coating procedure was determined with fresh Gram's iodine which wetted and stained (blue-black) the glycan-coated areas only.

With a second Pasteur pipette, the chitosan acetate-coated lumen of the tube was wetted with a solution of 5 mg/ml alpha-keratose solution prepared in a manner analogous to Example 1; the tubing was then allowed to dry again.

The resulting dried, coated tubing was then used as a substrate for live cell culture. Canine endothelial cells were grown on the chitosan keratinate membrane-coated PTFE in Roswell Park Memorial Institute (RPMI) 1640 tissue culture medium (MA bioproducts, Walkersville, MD). The cells spread more rapidly on such coated PTFE than on uncoated PTFE controls. See Sobinsky, K. R., D. P. Flanigan, A. Widra, J. P. Meyer, and J. J. Castronuovo, Surgical Forum 35:435–436(1984).

In order to reduce thrombogenicity in the prosthesis, heparin sodium may be dissolved in the alpha-keratose solution used to wet down and bind the chitosan acetate component to the tube. (Heparin polymerizes directly with the chitosan acetate solution and therefore makes uniform dispersion in chitosan acetate solutions difficult).

I claim:

1. A hydrophilic biopolymeric copolyelectrolyte comprising (a) a water-soluble linear anionic protein polyelectrolyte component derived from keratin, and (b) a water-soluble linear cationic biopolymer polyelectrolyte component derived from at least one biopolymer selected from the group consisting of a glucosaminoglycan and collagen.

2. The copolyelectrolyte of claim 1 comprising an integral mixture of said anionic protein polyelectrolyte component and said cationic protein polyelectrolyte component.

3. The copolyelectrolyte of claim 1 comprising one or more layers of said anionic protein polyelectrolyte component, which anionic layers may be the same or different, alternated with one or more layers of cationic protein polyelectrolyte component, which cationic layers may be the same or different.

4. The copolyelectrolyte of claim 1, wherein said anionic protein polyelectrolyte component is ammonium keratinate.

5. The copolyelectrolyte of claim 4, wherein the keratin moiety of said ammonium keratinate is alpha-keratose.

6. The copolyelectrolyte of claim 1, wherein said glucosaminoglycan is chitosan.

7. The copolyelectrolyte of claim 1, wherein said cationic biopolymer polyelectrolyte component is a biopolymer carboxylate.

8. The copolyelectrolyte of claim 7, wherein said biopolymer carboxylate is a biopolymer acetate.

9. The copolyelectrolyte of claim 1, wherein the weight ratio of said anionic protein polyelectrolyte component to said cationic biopolymer polyelectrolyte component is within the range of from about 0.001:1 to about 16:1.

10. The copolyelectrolyte of claim 9, wherein the weight ratio of said anionic protein polyelectrolyte component to said cationic biopolymer polyelectrolyte component is within the range of from about 0.001:1 to about 7:1.

11. The copolyelectrolyte of claim 10, wherein the biopolymer moiety of said cationic biopolymer polyelectrolyte component is a mixture of chitosan and collagen in a chitosan to collagen weight ratio of from about 0.5:1 to about 13:1.

12. A composition comprising the copolyelectrolyte of claim 1, and a flexibility-and/or adhesion-enhancing amount of a non-toxic plasticizer or softener.

13. The composition of claim 12, wherein said plasticizer or softener is glycerol.

14. A composition comprising the copolyelectrolyte of claim 1, and an antibiotic.

15. A composition comprising the copolyelectrolyte of claim 1 in powder form.

16. A hydrogel comprising the copolyelectrolyte of claim 1 in hydrated form.

17. A membrane comprising at least one layer of the hydrogel of claim 16, said membrane having a thickness of at least about 1 mil.

18. The membrane of claim 17, wherein both cationic chitosan and cationic collagen are present either in the same hydrogel layer or in two separate hydrogel layers.

19. A biodegradable dressing for burn wounds and other denuded tissure wound sites, comprising the membrane of claim 17.

20. The dressing of claim 19, wherein said membrane includes a flexibility-and/or adhesion-enhancing amount of a non-toxic plasticizer or softener.

21. The dressing of claim 20, wherein said plasticizer or softener is glycerol.

22. The dressing of claim 19, wherein said membrane includes an antibiotic.

23. A method for applying the dressing of claim 19 onto the wound site, wherein formation of said hydrogel is effected in situ on the wound site.

24. The method of claim 23, wherein said copolyelectrolyte is preformed and applied to said wound site in dehydrated form.

25. The method of claim 23, wherein said anionic protein polyelectrolyte component and said cationic biopolymer polyelectrolyte component are individually applied to said wound site.

26. The method of claim 25, wherein at least one of said two components is applied to said wound site as an aqueous solution.

27. The method of claim 26, wherein one of said two components is applied to said wound site in solid form.

28. The method of claim 27, wherein said solid form includes a flexibility-and/or adhesion-enhancing amount of a non-toxic plasticizer or softener.

29. The method of claim 28, wherein said component applied in solid form comprises chitosan acetate, and said plasticizer or softener is glycerol.

30. A method for applying the dressing of claim 19 onto the wound site wherein said hydrogel is preformed and applied to the wound site as a self-annealing paste.

31. A biodegradable lining for surgical prostheses, comprising the copolyelectrolyte of claim 1.

32. The method of claim 24, wherein said copolyelectrolyte is applied to said wound site in powder form.

33. A method of preparing a biodegradable dressing for burn wounds and other denuded tissue wound sites, comprising forming a membrane of at least one layer of a hydrophilic biopolymeric copolyelectrolyte including (a) a water-soluble linear anionic protein polyelectrolyte component derived from keratin, and (b) a water-soluble linear cationic biopolymer polyelectrolyte component derived from at least one biopolymer selected from the group consisting of glucosaminoglycan and collagen.

34. The method of claim 33 wherein a solution of said anionic protein polyelectrolyte component and a solution of said cationic biopolymer polyelectrolyte component are mixed together and the resulting mixture is allowed to dry down to form said membrane.

35. The method of claim 33 comprising preparing a membrane of a cationic biopolymer polyelectrolyte component and spraying said membrane with a solution of an anionic protein polyelectrolyte component.

36. The method of claim 33 further comprising the step of dehydrating said copolyelectrolyte membrane.

37. The method of claim 36, further comprising the step of reducing said dehydrated copolyelectrolyte membrane to a powder or granular form.

38. The method of claim 37, wherein said powder or granular dehydrated copolyelectrolyte membrane is rehydrated prior to use.

39. The method of claim 37, wherein said powder or granular dehydrated copolyelectrolyte membrane is applied to the wound site and allowed to rehydrate in situ.

* * * * *

UNITED STATES PATENT AND TRADEMARK OFFICE
CERTIFICATE OF CORRECTION

PATENT NO. : 4,570,629
DATED : February 18, 1986
INVENTOR(S) : Abe Widra

It is certified that error appears in the above—identified patent and that said Letters Patent is hereby corrected as shown below:

Col. 4, line 26: "maass" should read -- mass --.

Col. 5, line 16: "crystalline" should read -- crystallite --.

Col. 8, line 32: insert a comma after "protein" and before "centrifugation".

Col. 8, line 58: "Fifty mg" should read -- Fifty ml --.

Col. 10, line 37: "4 µg" should read -- 4 g --.

UNITED STATES PATENT AND TRADEMARK OFFICE
CERTIFICATE OF CORRECTION

PATENT NO. : 4,570,629

DATED : February 18, 1986

INVENTOR(S) : Abe Widra

It is certified that error appears in the above-identified patent and that said Letters Patent is hereby corrected as shown below:

Col. 14, line 6, "enterocci" should read -- enterococci --.

Signed and Sealed this

Eighth Day of July 1986

[SEAL]

Attest:

DONALD J. QUIGG

Attesting Officer

Commissioner of Patents and Trademarks